United States Patent [19]

Saukaitis et al.

[11] Patent Number: 5,808,067

[45] Date of Patent: Sep. 15, 1998

[54] PROCESS FOR PREPARING PYRIDINE AND QUINOLINE DERIVATIVES

[75] Inventors: John Saukaitis, East Grenwich, R.I.; Franklin B. Gupton, Petersburg, Va.

[73] Assignee: Hoechst Celanese Corporation, Somerville, N.J.

[21] Appl. No.: 361,908

[22] Filed: Dec. 21, 1994

Related U.S. Application Data

[63] Continuation-in-part of Ser. No. 507,330, Apr. 10, 1990, abandoned, and a division of Ser. No. 676,683, Mar. 28, 1991, Pat. No. 5,405,987, which is a continuation-in-part of Ser. No. 403,277, Aug. 31, 1989, abandoned.

[51] Int. Cl.$^6$ ...................... C07D 215/20; C07D 215/12; C07D 403/00; C07D 215/16
[52] U.S. Cl. .......................... 544/295; 544/296; 544/333; 546/86; 546/87; 546/156; 546/159; 546/168; 546/169; 546/170
[58] Field of Search ...................................... 546/168, 170, 546/156, 81, 86, 87, 159; 544/295, 296, 333

[56] References Cited

U.S. PATENT DOCUMENTS 4,675,432   6/1987   Maulding ................................ 596/170

OTHER PUBLICATIONS

Maulding, Chemical Abstracts, vol. 104, No. 128,845, "Prep. of anilinofumarate & quinoline–2,3–dicarboxylic acid", 1988.

Khandual et al, Chemical Abstract vol. 104, No. 224,414, "Reduction of nitro arenes by palladium(II) complexes", 1985.

Yang et al, Chemical Abstracts vol. 109, No. 73073 "The self oxidation of N–arylhydroxylamines", 1987.

Stradins, Chemical Abstract vol. 82 No. 23663 "Polarographic reduction of p–nitrophenol", 1974.

*Primary Examiner*—Alan L. Rotman
*Assistant Examiner*—Raymond Covington
*Attorney, Agent, or Firm*—Scott E. Hanf

[57] ABSTRACT

The present invention pertains to a method of preparing substituted and unsubstituted N-hydroxy-2-aminobutane diacid derivatives which can be dehydrated to 2-aminobut-2-ene dioic acid derivatives, which can be subsequently converted to pyridine and quinoline derivatives.

9 Claims, No Drawings

5,808,067

PROCESS FOR PREPARING PYRIDINE AND QUINOLINE DERIVATIVES

This is a divisional of application(s) Ser. No. 07/676,683 filed on Mar. 28, 1991 now U.S. Pat. No. 5,405,987 which is a cont.-in-part of U.S. patent application Ser. No. 07/403,277 filed Aug. 31, 1989, now abandoned, and a continuation-in-part of co-pending application Ser. No. 07/507,330 of Elango et al., filed Apr. 10, 1990, now abandoned.

BACKGROUND OF THE INVENTION

1. Field of the Invention

The present invention pertains to a method preparing substituted and unsubstituted N-hydroxy-2-aminobutane diacid derivatives which can be dehydrated to 2-aminobut-2-ene dioic acid derivatives, which subsequently can be converted to pyridine and quinoline derivatives. Unsubstituted hydroxylamines are reacted with substituted or unsubstituted unsaturated diacid derivatives to produce N-hydroxyaspartic acid derivatives which can be dehydrated to 2-aminobut-2-ene dioic acid derivatives, which can subsequently be reacted with α,β-unsaturated carbonyl compounds to produce pyridine derivatives. When the hydroxylamine is substituted, with a phenyl group, for example, so that N-phenyl-N-hydroxy-2-aminobutane dicarboxylic acid derivative is produced, this derivative can be dehydrated to form 2-anilinobut-2-ene dicarboxylic acid derivative which can further reacted with a Vilsmeier reagent such as an immonium salt to produce quinoline derivatives.

2. Background Art

N-hydroxyamino acids are valuable precursors for natural amino acids, peptides, herbicides, antibiotics, growth promoting agents, antitumor agents, antifungal agents, and polymers. It has been known that the addition of hydroxylamine to an unsaturated monocarboxylic acid derivative can be used to obtain N-hydroxyamino mono carboxylic acid derivative. However, addition of hydroxylamine to an unsaturated dicarboxylic acid, such as fumaric acid, in the presence of an enzyme does not successfully result in the isolation of N-hydroxyaspartic acid, as reported in "Progress in the Chemistry of Organic Natural Products", L. F. Alves et al., Springer-Verlag (1988), page 230. Indeed, the utilization of enzyme extracts, such as Bacillus caderas or Proteus vulgaris also does not yield success in isolating this desired product, but resort must be made, through utilization of a benzyl group, to protect the hydroxylamine moiety as reported by Kolasa, Can. J. Chem., Vol. 63, 2139 (1985). Such methods are cumbersome and involve the removal of protecting groups rather than employing hydroxylamine or a salt thereof directly.

K. Bashceruddin et al., Synthetic Communications, 9, 705–712 (1979) reports the questionable result of obtaining of N-hydroxyaspartic acids of greatly different melting points from maleic acid and fumaric acid, utilizing hydroxylamine. The reaction conditions for such conversion(s) are not disclosed, nor is revealed the criticality involved for obtaining N-hydroxyaspartic acid or its derivatives, namely a critical pH. Furthermore, the only relevant reaction conditions revealed in this publication, those for preparation of N-hydroxy-3-amino-3-(p-nitrophenyl)propionic acid from p-nitrocinnamic acid, do not yield N-hydroxyaspartic acid.

Literature methods for preparing 5,6-dialkyl and 5-alkyl-6-arylpyridine-2, –3-dicarboxylic acids and esters are limited and often require oxidation of alkyl or aryl substituents at positions 2 and 3 in order to obtain diacids. Recently there has been disclosed a method for the preparation of substituted and disubstituted pyridine-2,3-dicarboxylic acid esters and 2-alkylnicotinates utilizing α-halo-β-ketoesters and α,β-unsaturated aldehydes or ketones in the presence of an ammonium salt. The use of α-halo-β-ketoesters is not desired due to the fact that such materials are usually costly and unstable.

U.S. Pat. No. 4,723,011 discloses preparation of substituted and disubstituted pyridine-2,3-dicarboxylates by the reaction of an α-halo-β-ketoester such as chloro-diethyloxaloacetate (chloro-DOX) and an α,β-unsaturated aldehyde or ketone such as 2-ethylacrolein in the presence of at least 2 molar equivalents of an ammonium salt in order to produce the desired compounds.

U.S. Pat. No. 4,816,588 discloses and claims a process for preparing pyridine-2,3-dicarboxylic acids by the oxidation of 8-substituted quinolines.

European Patent Application No. 274,379 published Jul. 13, 1988 discloses two processes for producing pyridine-2,3-dicarboxylic acid compounds. One process seems similar to that previously described in U.S. Pat. No. 4,723,011 and the other process involves reacting an α,β-unsaturated aldehyde or ketone with various arninomaleates or aminofumarates such as diethyl aminomaleate.

European Patent Application No. 299,362 published Jan. 18, 1989 also discloses the same reaction.

U.S. Pat. No. 4,675,432 to Donald R. Maulding, issued Jun. 23, 1987 describes a method for the preparation of anilinofumarate. A dichlorosuccinate is reacted with a molar equivalent of aniline in an inert organic solvent and with two or more molar equivalents of an aqueous base in the presence of a phase transfer catalyst to produce the anilinofumerate.

U.S. Pat. No. 4,656,283 to Robert F. Doehner, Jr., issued Apr. 7, 1987 describes a method for the preparation of alkyl esters of substituted 2-methyl -quinoline-3-carboxylic acid and quinoline-2,3-dicarboxylic acid as well as dialkyl 3-(substituted)-phenylaminobut-2-ene-dioates. An appropriately substituted aniline is reacted with approximately an equimolar amount of a keto-ester to produce the products above-described.

Although the methods described above are useful for producing some of the reaction products produced by the method of the present invention; due to the broad utility of the reaction products of the present invention, as nutrient supplements, and as intermediaries in the production of pharmaceuticals, dyes and pigments and herbicides, any improvement in the method of production is of tremendous potential economic significance.

SUMMARY OF THE INVENTION

The present invention pertains to a method of preparing substituted and unsubstituted N-hydroxy-2-aminobutane diacid derivatives which can be dehydrated to 2-aminobut-2-ene dioic acid derivatives, which subsequently can be converted to pyridine and quinoline derivatives. An unsubstituted hydroxylamine is reacted with an substituted or unsubstituted unsaturated diacid derivative to produce N-hydroxyaspartic acid derivatives which can be dehydrated to 2-aminobut-2-ene dioic acid derivatives, which can subsequently be reacted with α,β-unsaturated carbonyl compounds to produce pyridine derivatives. In the alternative, a single pot reaction can be carried out wherein the unsubstituted hydroxyl amine is contacted with a substituted or unsubstituted unsaturated diacid derivative, followed by a dehydration technique, with subsequent addition of the α,β-unsaturated carbonyl compound, to produce the pyridine derivative directly (without isolation of the 2-aminobut-2-ene dioic acid derivative formed upon the dehydration step).

In addition, when the hydroxylamine is substituted with a phenyl group so that N-phenyl-N hydroxy-2-aminobutane dicarboxylic acid is produced, this derivative can be dehydrated to produce substituted and unsubstituted 2-anilinobut-2-ene dicarboxylic acid derivative which can be further reacted with a Vilsmeier reagent to produce quinoline derivatives.

The chemical formulae representing the above-described method are shown below:

I. Synthesis of N-Hydroxy-2-aminobutane Diacid Derivatives

In accordance with the present invention, in preparation of the substituted and unsubstituted N-hydroxy-2-aminobutane diacid derivatives, it was discovered that the pH of the reaction medium is critical, and should range from about 5 to about 12 and preferably from about 6.5 to about 9. In addition, the present invention permits reaction at ambient temperatures (about 25° C.) to about 80° C., whereby reaction products which tend to be thermally unstable at higher temperatures are preserved.

The reaction is represented by the following formulae:

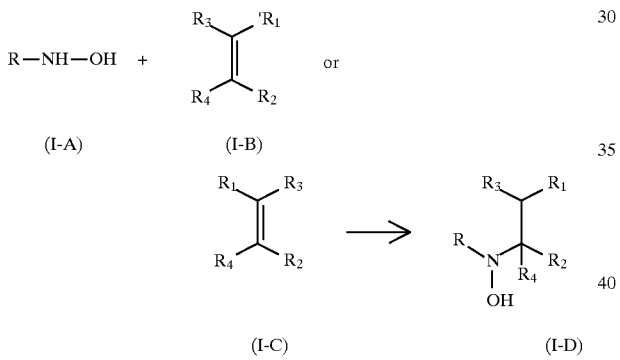

wherein: R=H, alkyl (preferably $C_1$–$C_6$ straight or branched), substituted or unsubstituted aryl (preferably phenyl or naphthyl), and wherein the substituents are selected from alkyl, alkoxy, carboxy, halogen, cyano, and nitro;

$R_1$ and $R_2$=each independently, $$\underset{C-Z,}{\overset{O}{\|}}$$

wherein Z is $OR_5$ or $NR_5R_6$; or CN; or $R_1$ and $R_2$ together is $$\underset{C-NR_7-C;}{\overset{O\quad\quad O}{\|\quad\quad\|}}$$

$R_3$ and $R_4$ are each independently H; alkyl; halogen; CN; substituted and unsubstituted aryl (preferably phenyl and naphthyl) wherein the substituents are selected from alkyl, arylalkyl, alkoxy, carboxy, halogen, nitro, and cyano;

$$\underset{C-Z,}{\overset{O}{\|}}$$

wherein Z is defined as above;

$R_5$ and $R_6$ are each independently H, alkyl (preferably $C_5$–$C_6$ straight or branched), aryl (preferably phenyl), arylalkyl (preferably aryl $C_5$–$C_6$ alkyl); or $R_5$ and $R_6$ together with the nitrogen atom form a heterocyclic substituent, selected from pyrrolidinyl, piperidinyl, imidazolidyl, hydrogenated pyrimidinyl, including dihydro-, tetrahydro-, and hexahydropyrimidinyl; and $R_7$ is H, alkyl (preferably $C_5$–$C_6$ straight or branched), substituted or unsubstituted aryl (preferably phenyl), or an alkoxy of 1–6 carbon atoms.

II. Conversion of the N-Hydroxy-2-aminobutane Diacid Derivative to a 2-Aminobut-2-ene Dioic Acid Derivative with Subsequent Conversion to Nitrogen-Comprising Aromatic Compounds Compounds I—D are used in a second embodiment of this invention, wherein Compounds I—D are subjected to dehydration to produce 2-aminobut-2-ene dioic acid derivatives, Collective Compound II.

Compound II—A, Compound II—B or the tautomer Compound II—C which have the formulae respectively, wherein R is as described above and wherein R' is R1, R" is R2, and R''' is R4, or R' is R2, R" is R1, and R''' is R3 including all the geometric isomers of Compounds IIA and IIB, including the compounds (Compounds II—A, II—B, II—C and the geometric isomers of Compounds II—A and II—B are hereinafter collectively referred to as Collective Compound II).

In another embodiment of the present invention, Collective Compound II, when R is H and $R_3$ and $R_4$ are H or halogen, can be reacted with α,β-unsaturated carbonyl compounds of the formula II-D

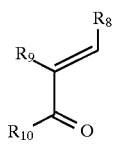

(II-D)

wherein $R_8$ and $R_{10}$=H, alkyl or alkenyl (preferably $C_1$–$C_6$ straight or branched) or substituted or unsubstituted aryl (preferably phenyl or naphthyl), wherein the substituents are selected from alkyl, alkoxy, carboxy, carboalkoxy, halogen, and cyano;

wherein $R_9$=the same as $R_8$ and $R_{10}$, but also including halogen, and wherein $R_9$ and $R_{10}$ taken together can be—$(CH_2)$—$_{3-10}$; to produce pyridine derivative of the Formula II—E

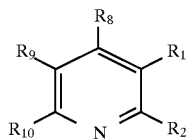

(II-E)

wherein $R_8$, $R_9$, and $R_{10}$ are as described above. Particular embodiments of the conversion of specific compounds included in Collective Compounds II to specific compounds included in Compound II—E, wherein $R_8$, $R_9$, and $R_{10}$ substituents are as revealed and defined as corresponding substituents $R_1$, $R_2$, $R_3$, and $R_6$ of U.S. Pat. No. 4,758,667, incorporated by reference hereinto in its entirety.

Compound II—E, in turn, is a precursor in the synthesis of Compound II—F of the formula

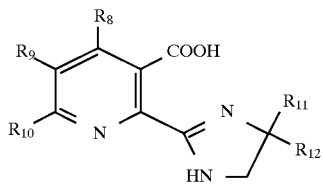

(II-F)

wherein $R_{11}$ and $R_{12}$ are each independently of the other $C_1$–$C_6$ alkyl, as revealed and defined as corresponding to substituents $R_4$ and $R_5$ in U.S. Pat. No. 4,758,667, incorporated hereinto by reference. Compound II-F has herbicidal properties and can be used for controlling undesired plant growth.

Throughout the specification and appended claims, a given chemical formula or name shall encompass all geometric, optical isomers and racemic mixtures thereof where such isomers exist.

In the above definitions, the term "aryl" refers to a monovalent substituent which consists of an aryl group, e.g. phenyl, o-toluyl, m-methoxyphenyl, etc., of the formula

where X is hydrogen, halogen, lower alkyl, lower alkoxy, $CF_3$, and $NO_2$ and n is an integer of 1 to 5; the term "arylalkyl" refers to a monovalent substituent which consists of an aryl group, e.g. phenyl, o-toluyl, m-methoxyphenyl, etc., linked through an alkylene group having its free valence bond from a carbon of the lower alkylene group, and having a formula of -alkylene

where X and n are is as defined above; the term "alkylene" refers to a bivalent radical of the lower branched or unbranched alkyl group it is derived from having valence bonds from two terminal carbons thereof, e.g. ethylene ($—CH_2CH_2—$), propylene ($—CH_2CH_2CH_2—$), isopropylene

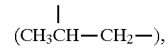

etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.

In the alternative:

III. Single Pot Formation of the Pyridine Derivative from Substituted or Unsubstituted Diacid Derivatives, Unsubstituted Hydroxylamine, and α, β-Unsubstituted Carbonyl Compounds

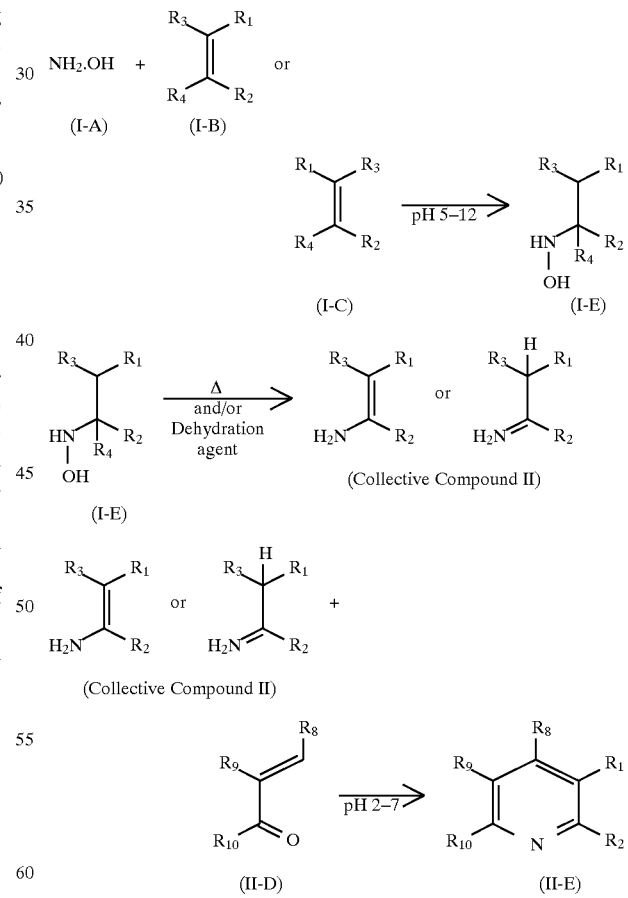

wherein: R=H;

$R_1$ and $R_2$=each independently H, alkyl (preferably $C_1$–$C_6$ straight or branched), aryl (preferably substituted or unsubstituted phenyl or naphthyl), COZ, or CN, provided both are not H, and wherein Z=$OR_5$ or $NR_5R_6$, wherein $R_5$ and $R_6$ are as described above; or $R_1$ and $R_2$ are together —CO—$NR_1$—CO, wherein $R_1$ is as described above.

$R_3$ and $R_4$ of Collective Compound II=H, or halogen;

$R_8$ and $R_{10}$ are as described above;

$R_9$ and $R_8$ and $R_9$ taken together are as described above.

The expression substituted-aryl preferably is intended to mean phenyl or naphthyl substituted in one or more positions with halogen (bromine, chlorine, fluorine or iodine); $C_1$–$C_6$ alkyl; alkoxy of 1–6 carbon atoms, cyano, nitro, or carboxy.

The α,β-unsaturated carbonyl compounds are preferably aldehyde or ketone wherein $R_8$, $R_9$, and $R_{10}$ are as described above.

The acetal and ketal derivatives of the carbonyl compounds, or the Mannich base equivalent to such carbonyl compounds can also be used in the invention.

IV. Preparation of Quinoline Derivatives by Reacting a Substituted or Unsubstituted Phenylhydroxyamine with a Substituted or Unsubstituted Unsaturated Diacid Derivative to Form a Phenylhydroxylamine Adduct, Dehydrating to Form Substituted and Unsubstituted 2-Anilino-But-2-Ene Dicarboxylic Acid Derivative, Followed by Reaction with Vilsmeier Reagent to Form a Quinoline Derivative

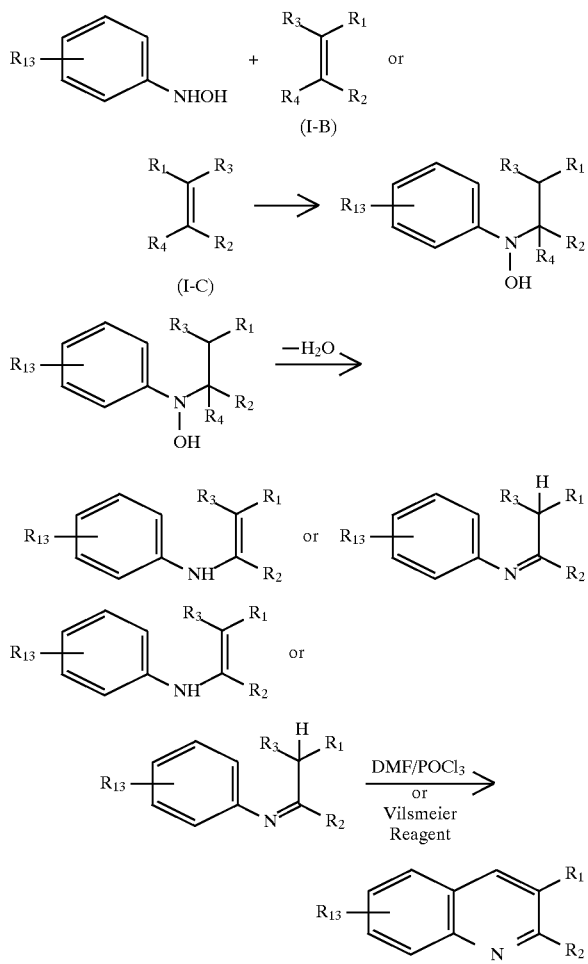

wherein $R_1$, $R_2$, $R_3$, and $R_4$ are as described in Section III above;

wherein $R_{13}$ is H, alkyl (preferably $C_1$–$C_6$ straight or branched, aryl (preferably phenyl or naphthyl), alkoxy, halogen, cyano, carboalkoxy, thioalkoxy, or $CF_3$.

DETAILED DESCRIPTION

More specifically, the preferred embodiments of the above-described method follow. Throughout the specification and appended claims, a given chemical formula or name shall encompass all geometric, optical isomers and racemic mixtures thereof where such isomers exist.

I. Synthesis of N-Hydroxy-2-aminobutane Dicarboxylic Acid Derivatives

The present invention is described in terms of synthesizing esters of N-hydroxyaspartic acid and esters of 2-aminobut-2-ene dioic acids, such as dialkyl 2-aminomaleate. However, it should be understood that such description is exemplary only and is for purposes of exposition and not for purposes of limitation. It will be readily appreciated that the inventive concept described is equally applicable to both substituted and unsubstituted N-hydroxyaspartates as well as esters which are alkyl or aryl.

This embodiment of the present invention relates to a method of synthesizing a N-hydroxyaspartic acid derivative of the formula:

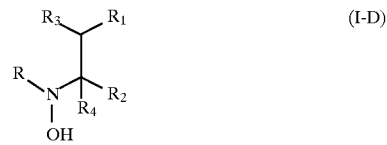

where $R_1$ and $R_2$ are each independently

where Z is $OR_5$ or $NR_5R_6$ where $R_5$ and $R_6$ are each independently H, alkyl (preferably $C_1$–$C_6$ alkyl branched or straight), aryl (preferably phenyl or naphthyl), arylalkyl, or $R_5$ and $R_6$ together with the nitrogen atom form a heterocyclic substituent, selected from pyrrolidinyl, piperidinyl, imidazolidyl, hydrogenated pyrimidinyl, including dihydro-, tetrahydro-, and hexahydropyrimidinyl; CN, or $R_1$ and $R_3$ together is

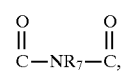

where $R_7$ is as defined above; and $R_3$ and $R_4$ are each independently H, alkyl (preferably $C_1$–$C_6$ alkyl branched or straight), aryl (preferably phenyl or naphthyl), arylalkyl,

where Z is as defined above; CN, and halogen.

The term "alkyl" refers to a straight or branched chain hydrocarbon of 1 to 18 carbon atoms containing no unsaturation, e.g. methyl, ethyl, isopropyl, 2-butyl, neopentyl, n-hexyl, n-heptyl, n-nonyl, etc.; the term "aryl" refers to a monovalent substituent which consists of an aryl group, e.g. phenyl, o-toluyl, m-methoxyphenyl, etc., of the formula

where X is hydrogen, halogen, lower alkyl, lower alkoxy, $CF_3$, and $NO_2$, and n is an integer of 1 to 5; the term "arylalkyl" refers to a monovalent substituent which consists of an aryl group, e.g. phenyl, o-toluyl, m-methoxyphenyl, etc., linked through an alkylene group having its free valence bond from a carbon of the lower alkylene group, and having a formula of -alkylene

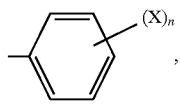

where X and n are is as defined above; the term "alkylene" refers to a bivalent radical of the lower branched or unbranched alkyl group it is derived from having valence bonds from two terminal carbons thereof, e.g. ethylene ($—CH_2CH_2—$), propylene ($—CH_2CH_2CH_2—$), isopropylene, etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.

The synthesis of N-hydroxyaspartic acid derivative (Compound I-D, when R is H) is made in the following manner. The substituents $R_1$, $R_2$, $R_3$, $R_4$, $R_5$, $R_6$, and Z are as defined above unless indicated otherwise.

A suitable diacid derivative of the formula

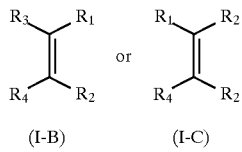

is selected. Such diacid derivatives are well known or can be synthesized using conventional techniques well known to those of ordinary skill in the art. Compound I—B or I—C is reacted with substituted hydroxylamine R—NH—OH or with unsubstituted hydroxylamine, H—NH—OH, or a suitable salt thereof, to produce N-hydroxyaspartic acid derivative. For purposes of simplification, subsequent descriptions will be limited to unsubstituted hydroxylamine, although it is understood the hydroxylamine can be substituted as well. A suitable hydroxylamine salt includes a mineral acid salt such as hydroxylamine hydrochloride, hydroxylamine sulfate, hydroxylamine bisulfate, hydroxylamine phosphate etc. or an organic acid salt, e.g. hydroxylamine acetate, etc. The reaction may be carried out with or without a suitable solvent. If carried out in a solvent, a suitable solvent includes water, a lower alkanol, e.g. methanol, ethanol, isopropanol, 1-butanol, etc.; a halogenated lower hydrocarbon or alkane e.g. dichloromethane, chloroform, carbontetrachloride, dichloromethane etc.; an aromatic hydrocarbon, e.g. benzene, toluene, etc.; an ether, e.g. ethylether, dioxane, tetrahydrofuran, etc.; an ester, e.g. ethyl acetate, isopropyl acetate, butyl acetate, etc.; and an aprotic solvent, e.g. acetonitrile, dimethylformamide, dimethylsulfoxide, etc; and mixtures thereof.

It is critical that the reaction be conducted under weakly acidic to basic conditions (pH=5–12) since it has been found that when the corresponding dicarboxylic acid of Compound I—B or I—C is employed, e.g. maleic acid or fumaric acid, addition of the hydroxylamine across the double bond leading to the N-hydroxyaspartic acid does not occur. Additionally, where the reaction between Compound I—B or I—C and the hydroxylamine or its salt is conducted under more acidic pH conditions, the desired reaction again does not occur to yield the N-hydroxyaspartic acid derivative. The reaction must be carried out under critical pH conditions which are at most weakly acidic, i.e. the upper acid pH range being weakly acid, that is, at a pH region of 5 through about 12, preferably a pH range of about 6.5 to about 9.

During the reaction of hydroxylamine with Compound I—B or I—C, the hydroxylamine itself provides the basic medium. When a hydroxylamine salt is used, a suitable base should be employed to achieve the critical pH reaction condition. A suitable base is one selected from an inorganic base, e.g. sodium hydroxide, potassium hydroxide, ammonium hydroxide, sodium carbonate, potassium carbonate etc.; an organic base, e.g. pyridine, triethylamine, sodium methoxide, etc., present in an amount ranging from about 1 to about 3 moles of base to one mole of hydroxylamine salt, and preferably from 1 mole of base per one mole of hydroxylamine salt, except in the case of a hydroxylamine salt of a diprotic acid, such as hydroxylamine sulfate, wherein 2 moles of base per mole of salt is preferred.

It is to be understood that pH values, resulting when there are solvent levelling effects involved, which correspond to the above-identified critical pH range are equally applicable.

Compound I—B or I—C and the hydroxylamine or its salt, are employed in a mole ratio ranging from about 1:1 to about 1:3, with the preferred mole ratio being between 1:1 to 1:1.5 of Compound I—B or I—C to the hydroxylamine or its salt.

Typically the reaction, conducted with the mole ratios of Compound I—B or I—C, hydroxylamine or its salt, and base, as indicated above, is carried out at a temperature ranging between about –10° C. to about 80° C., preferably about 10° C. to about 50° C., for a time period ranging from about 0.1 to about 15 hours to obtain addition of the $NH_2OH$ (or RNHOH) across the carbon-carbon double bond of Compound I—B or I—C, typically following Markovnikov's rule, to obtain Compound I—E (or Compound I—D).

Compound I—E includes, but is not limited to, dimethyl N-hydroxyaspartate, diethyl N-hydroxyaspartate, dipropyl N-hydroxyaspartate, di-iso-propyl N-hydroxyaspartate, di-n-butyl N-hydroxyaspartate, N-hydroxyaspartonitrile and triethyl 2-(N-hydroxyamino)-ethanetricarboxylate.

If Compound I—D is an ester, of course it can be hydrolyzed, using conventional techniques, to obtain the free acid, i.e.

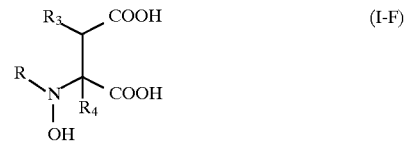

The examples which follow are for purposes of illustrating the embodiment of the present method described under I above, and are not to be construed as limiting the invention disclosed herein.

EXAMPLE 1

Diethyl N-Hydroxyaspartate

Hydroxylamine free base (50% aqueous solution, 45.0 g, 0.68 mol) was added dropwise to diethyl maleate (100.0 g, 0.56 mol) under nitrogen. The reaction temperature was maintained below 55° C. with an ice bath. The mixture was stirred for 30 minutes. Dichloromethane (100 ml) was added to the reaction mixture and the organic layer was collected. The organic layer was concentrated under reduced pressure to give crude diethyl N-hydroxyaspartate (103 g, 89% yield). The product was analyzed by NMR spectroscopy and found to be greater than 95% pure.

EXAMPLE 2

Diethyl N-Hydroxyaspartate

Sodium hydroxide (40% aqueous solution, 12.9 g, 0.129 mol) was added over 20 minutes to a stirred mixture of diethyl maleate (17.3 g, 0.1 mol) and hydroxylamine sulfate (25% aqueous, 39.0 g, 0.059 mol) during which the reaction temperature rose from 28° C. to 53° C. The reaction mixture was stirred for 30 minutes under nitrogen. The mixture was transferred to separating funnel, methylene chloride was added (50 ml), the organic layer was collected and concentrated to give diethyl N-hydroxyaspartate (18.5 g, 0.99 mol, 90% yield).

EXAMPLE 3

Diethyl N-Hydroxyaspartate

Sodium hydroxide solution (50% aqueous, 96.0 g, 1.2 mol) was added over 30 minutes to an aqueous solution of hydroxylamine sulfate (25%, 394.2 g, 0.6 mol). The temperature was kept below 40° C. during the caustic addition. The reaction pH was about 9 at the end of caustic addition. Diethyl maleate (172.0 g, 1.0 mol) was then added to the reaction and stirred for 60 minutes at which time the pH was about 7.4. The reaction mixture was transferred to a separatory funnel, the layers were allowed to separate, and the organic phase containing diethyl N-hydroxyaspartate was separated. The crude product was analyzed by NMR and found to be >90% pure (207 g).

EXAMPLE 4

Preparation of Diethyl N-hydroxyaspartate

Hydroxylamine Free base (50% aq. soln., 45.0 g, 0.68 mol) was added dropwise to a solution of diethyl maleate (100.0 g, 0.56 mol) in ethanol (100 mL) in a 3-neck flask blanketed with nitrogen. The reaction temperature was maintained below 55° C. with an ice bath. The mixture was stirred for 30 minutes. The reaction mixture was concentrated under reduced pressure to give crude diethyl N-hydroxyaspartate (103 g, 89% yield). The product was analyzed by nuclear magnetic resonance spectroscopy (NMR) and shown to be at least 95% pure. NMR (acetone-d6) 1.20 (m, 6H), 2.59 (dd, J 6.8, 16.1 Hz, 1H), 2.76 (dd, J 6.8, 16.1 Hz, 1H), 3.89 (t, J 6.8 Hz, 1H), and 4.11 (m, 4H).

EXAMPLE 5

Dimethyl N-Hydroxyaspartate

Hydroxylamine free base (50% aqueous solution, 7.3 g, 0.11 mol) was added over a 30 minute period to dimethyl maleate (15.0 g, 0.1 mol) under nitrogen. The reaction temperature was maintained below 55° C. with an ice bath. The mixture was stirred for 30 minutes. The reaction mixture was added to dichloromethane (200 ml) and the organic phase was separated. The organic phase was dried with magnesium sulfate and concentrated to give dimethyl N-hydroxyasparate (16.2 g, 90% yield).

EXAMPLE 6

Dibutyl N-Hydroxyaspartate

Hydroxylamine free base (50% aqueous solution, 8.0 g, 0.12 mol) was added dropwise to dibutyl maleate (25.0 g, 0.1 mol) in a 3-neck 250 ml flask blanketed with nitrogen. The reaction temperature was maintained below 55° C. with an ice bath. The mixture was stirred for 30 minutes. The gas liquid chromatography (GLC) analysis of the reaction mixture indicated 96% conversion of dibutyl maleate. The NMR analysis showed that the reaction mixture contained dibutyl N-hydroxyaspartate in greater than 95% purity.

EXAMPLE 7

N-Hydroxyaspartonitrile

Hydroxylamine free base (50% aqueous solution, 2.0 g, 30.3 mmol) was added over 2 minutes to a suspension of fumaronitrile (2.0 g, 25.6 mmol) in ethanol (15.0 g). During the course of the hydroxylamine addition, the reaction temperature changed from 18° C. to 48° C. The reaction mixture was cooled to room temperature and stirred for one hour. The GLC analysis of the reaction mixture showed that the reaction proceeded with complete conversion of fumaronitrile to give N-hydroxyaspartonitrile in 90% selectivity. The solvent was removed and the product was characterized by NMR.

EXAMPLE 8

Triethyl 2-(N-hydroxyamino)-1,1,2-ethanetricarboxylate or Diethyl 3-(Carboethoxy)-N-hydroxyaspartate Triethyl ethenetricarboxylate (4.0 g, 16.3 mmol), obtained from diethyl malonate and ethyl glyoxalate; was dissolved in ethanol (25 g) and hydroxylamine (50% aqueous solution, 1.3 g, 19.6 mmol) was added to the reaction mixture. A solid precipitated out within 10 minutes indicating the completion of the reaction. The solvent was removed under reduced pressure to give the crude product. The crude product was analyzed by NMR and found to have triethyl 2-(N-hydroxyamino)ethanetricarboxylate.

II. Conversion of the N-Hydroxy-2-Aminobutane Diacid Derivative to a 2-Aminobut-2-ene Dioic Acid Derivative with Subsequent Conversion to Nitrogen-Comprising Aromatic Compounds Compound I—D, where at least either $R_3$ or $R_4$ is hydrogen can then be subjected to dehydration using conventional techniques well known to those skilled in the art to obtain a 2-aminobut-2-ene dioic acid derivative (Collective Compound II). The dehydration of Compound I—D can be affected by heating. This dehydration by heating can be conducted with or without a suitable dehydration agent. If a dehydration agent is employed, the agent is typically present in an amount ranging from about 0.1% to about 100% by weight, preferrably about 0.1% to about 10% by weight, to yield the 2-aminobut-2-ene dioic acid derivative.

Any dehydration agent known in the art can be employed. Some suitable dehydration agents include an inorganic acid catalyst, e.g. $H_2SO_4$, HCl, phosphoric acid, polyphosphoric acid, etc.; an ion exchange acidic resin, e.g. Amberlyst$^R$, Dowex$^R$, Nafion-H$^R$, etc.; an organic acid, e.g. p-toluenesulfonic acid, methanesulfonic acid, etc.; an inorganic base, e.g. potassium bicarbonate, sodium carbonate, etc.; an organic base, e.g. pyridine, triethylamine, etc.; a basic ion exchange resin, e.g. Amberlyst$^R$, Dowex$^R$, etc., or a transition metal catalyst, e.g. palladium, rhodium, etc.

Dehydration can also be carried out using acylation agents or a combination of acylation agent and an organic base of the kind described above. The acylation agents include carboxylic acid anhydride, e.g. acetic anhydride and trifluoroacetic anhydride; and acid chloride, e.g. acetyl chloride and propanoyl chloride.

Typically the dehydration, with or without suitable agent, can be carried out in a suitable solvent, e.g. water, alcohols, such as ethanol, butanol, hydrocarbons, such as heptane, parafins; halogenated hydrocarbons such as chloroform and methylene chloride; aromatic hydrocarbons such as toluene, xylene; ethers, polar aprotic solvents such as dimethylformamide, diglyme, tetraglyme, etc., at a temperature ranging from about 25° C. to about 300° C., preferably about 50° C. to about 200° C., for about 0.01 to about 48 hours, to obtain 2-aminobut-2-ene dioic acid.

Compound I—D is then dehydrated using heat and/or a dehydration agent, as shown under Section II, above to form Collective Compounds II which are subsequently reacted with an α,β-unsaturated carbonyl compound such as an aldehyde or ketone (Compound II—D).

The resultant Collective Compound II, represented in part by the compounds of the formulae as previously described on Pages 7 and 8

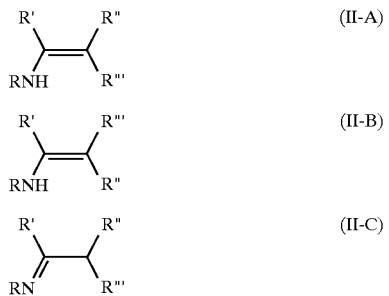

(II-A)

(II-B)

(II-C)

can be isolated. When R is H and when at least $R_3$ is hydrogen or halogen, then Collective Compound II can be reacted with a substituted α,β-unsaturated carbonyl compound of the formula

(II-D)

where $R_8$, $R_9$, and $R_{10}$ are as defined above (and which correspond to $R_1$, $R_2$ and $R_3$, respectively, of U.S. Pat. No. 4,758,667), to obtain a compound of the formula

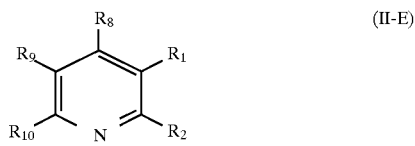

(II-E)

which includes 2,3-pyridinedicarboxylic acid derivatives such as 5-alkylpyridine-2,3- dicarboxylic acid.

The reaction between Collective Compounds II and those of Formula II—D is conveniently carried out by heating the same in the presence of an acid and suitable solvent preferably at reflux for periods of time ranging from 0.5 to 48 hours. Although the preferred temperature is at reflux, any temperature from ambient up to the boiling point of the solvent can be employed. A relative pH between 3–4 appears optimal although a pH ranging from 2–7 can be used.

The mole ratio of the compounds of Formula I—D to the aldehydes or ketones of Formula II—D is not critical and can range from about 1:3 to 3:1. It is preferred to use approximately from 1:1.0 to 1:1.3 molar ratios.

If desired a dehydrogenation catalyst can be added to the reaction mixture of Collective Compounds II and II—D, in order to aid in aromatization of the newly-generated ring. The dehydrogenation catalyst when employed is conventional in the art and includes metals or compounds of platinum, palladium, ruthenium, iridium, nickel, iron, copper, cobalt, rhodium, etc. The dehydrogenation metal or compound thereof deposited on a suitable support, such as alumina, carbon, clay, zeolites, chromia, zirconia, etc. A preferred dehydrogenation catalyst is palladium on carbon.

As has been previously stated, an acid is employed to provide an acidic pH range (from about 2 to about 7). Suitable acids include inorganic acids such as hydrochloric, phosphoric, sulfuric, etc. and preferably organic acids such as acetic, trifluoroacetic, p-toluenesulfonic, methanesulfonic, trifluoromethanesulfonic, propionic, butyric or other carboxylic acids including aromatic carboxylic acids. Ion-exchange resins such as Amberlyst$^R$, Dowex$^R$, NAFION$^R$ can also be used as acidic components.

When an acid is used which is also a solvent i.e. acetic acid, no additional solvent is required.

Solvents suitable for use during the reaction of Collective Compounds II with Compounds II—D include: water, alcohols, chlorinated hydrocarbons, hydrocarbons, aromatic hydrocarbons, ethers, organic acids, esters, and aprotic solvents such as acetonitrile. The preferred solvents are lower alkyl alcohols, such as methanol, ethanol, propanol, and butanol and aromatic hydrocarbons, such as benzene and toluene. Particularly preferred solvents are 1-butanol and/or ethanol.

Thus, pyridinecarboxylic acid derivatives containing substituents in the 4-,5-and 6- position may conveniently be prepared by dehydrating Formula I—D N-hydroxyamino derivatives to form at least one of the Collective Compound II compounds which is then admixed with a Formula II—D α,β-unsaturated aldehyde or ketone in the presence of an acid and preferably a solvent, and stirring the resulting reaction mixture at a temperature in the range of ambient temperature to the boiling point of the solvent, and preferably at reflux, until the reaction is essentially complete and isolating the formed 4-substituted, 4-5-disubstituted, 4,6-disubstituted, 5-substituted, 6-substituted or 5,6-disubstituted pyridine-2,3-dicarboxylic acid derivatives by standard laboratory techniques such as extraction, evaporation, distillation or column chromatography.

Compound II—E, which includes 2,3-pyridine carboxylic acid derivatives, can be reacted with a 2-aminoalkane carboxamide, as defined in U.S. Pat. No. 4,758,667, and reacted as described in this patent to form the 2-(imidazolin-2-yl)-3-pyridine carboxylic acids described therein.

The examples which follow are for purposes of illustrating the embodiment of the present method described under II above, and are not to be construed as limiting the invention disclosed herein.

EXAMPLE 9

Diethyl 3-Aminomaleate by Thermolysis

A solution (10 ml) of diethyl N-hydroxyaspartate (9.4% solution, 7.8 g, 3.6 mmol) in ethanol was fed in a quartz column (1 inch ID) containing glass beads (3 inches long) at 200° C. at the rate of 0.2 ml per minute along with nitrogen at a rate of 1000 ml per minute. The vaporized material escaping at the end of quartz column was collected using a dry-ice trap. The condensate (0.35 g) was analyzed by GLC. The analysis found that the reaction gave diethyl 2-aminomaleate in about 34.5% yield.

EXAMPLE 10

Diethyl 2-Aminomaleate using an Acid Dehydration Agent

Hydroxylamine free base (50% aqueous solution, 2.0 g, 30.3 mmol) was dropwise added to diethyl maleate (4.41 g, 25.6 mmol) and stirred for 60 minutes at 40°–45° C. to give diethyl N-hydroxyaspartate. Toluene (5.02 g) and p-toluenesulfonic acid (0.05 g, 0.26 mmol) were added to the reaction mixture and refluxed for 4.5 hours. The reaction mixture was analyzed by GLC, which showed that the reaction proceeded to give 89% diethyl 2-aminomaleate (80% yield based on the external standard).

EXAMPLE 11

Preparation of Diethyl 2-aminomaleate Using AceticAnhydride

Triethylamine (6.5 g, 64.4 mmol) was added dropwise to diethyl N-hydroxyaspartate (11.95 g, 58.3 mmol) and stirred at room temperature for 15 minutes. Acetic anhydride (6.58 g, 64.5 mmol) was then added dropwise to the reaction mixture while temperature was maintained below 40° C. using an ice bath. The reaction was stirred at room temperature for an hour and at 60–70° C. for another hour. The reaction was analyzed by GLC. The analysis found the reaction mixture to contain mainly diethyl 2-aminomaleate with about 10% of diethyl N-acetyl-2-aminomaleate.

EXAMPLE 12

Diethyl 2-Aminomaleate and Diethyl 2-Iminosuccinate

Hydroxylamine (50% aqueous solution, 2.05 g, 31.1 mmol) was added to a solution of diethyl maleate (4.3 g, 25.0 mmol) in ethanol (10 ml) at room temperature. The reaction mixture temperature increased to 70° C. within five minutes. The reaction mixture was cooled to room temperature and stirred for 48 hours. The GLC analysis showed that the reaction mixture contained 33% diethyl N-hydroxyaspartate, 32% diethyl 2-aminomaleate, and 21% diethyl 2-iminosuccinate.

EXAMPLE 13

Aminomaleate Conversion to 5-Ethylpyridine-2.3-Dicarboxylate

Acetic acid (10 ml) was added to a solution of diethyl 2-aminomaleate (18.7 g, 0.10 mol) in ethanol (38 ml) in a 250 ml flask. The reaction pH was measured and found to be 3.9. The reaction flask was equipped with a reflux condenser, thermometer, heating mantle, stirrer, and dropping funnels. Then, 2-ethylacrolein (12.8 g, 0.13 mol) was added all at once and the reaction mixture was heated to reflux for 3 to 5 hours. The solvent was removed on a vacuum rotary evaporator and the residue was vacuum distilled. The yield of diethyl 5-ethylpyridine-2,3- dicarboxylate was 13.8 g (55% of theoretical).

EXAMPLE 14

Aminomaleate Conversion to 5-Methylyridine-2.3-Dicarboxylate

Repeating the process described in Example 13 with 2-methylacrolein (10.9 g, 0.13 mol) gave 9.0 g (38% yield) of diethyl 5-methylpyridine-2,3-dicarboxylate.

III. Single Pot Formation of the Pyridine Derivative from Substituted or Unsubstituted Diacid Derivatives. Unsubstituted Hydroxylamine, and α, β-Unsaturated Carbonyl Compounds Another embodiment of the invention involves the single-pot preparation of substituted and disubstituted pyridinecarboxylates of Formula II—E by reacting a diacid derivative of Formula I—B or I—C:

wherein $R_1$ and $R_2$ are defined above with unsubstituted hydroxylamine of Formula (I—A) or a salt thereof, such as the hydrochloride, salt at ambient temperatures for periods of time ranging from about 30 minutes to about 3 hours at a pH ranging from about 6 to about 12. The resulting reaction product is then subjected to dehydration using heat or a dehydrating agent, or both, at temperatures ranging from about 25° C. to about 200° C., for a time period ranging from about 1 second to about 12 hours. After dehydration, an acid is added to lower the pH to 2–7, or preferably 3–4, and an α,β-unsaturated aldehyde or ketone of Formula II—D is added, and the reaction mixture is subjected to elevated temperatures ranging from about 50° C. to about 125° C. for periods of time ranging from about 1 to about 48 hours.

A preferred embodiment of the invention involves the preparation of substituted and disubstituted pyridinedicarboxylates of Formula II—F by treating a alkene of Formula I—B or I—C wherein $R_1$, and $R_2$ are defined above with a substituted or unsubstituted hydroxylamine or a mixture of a hydroxylamine salt and a base at a temperature of 15° C. to 60° C. for periods of 0.1 to 2 hours at a pH of 7–9. The resulting reaction product is then subjected to dehydration using heat or a dehydrating agent, or both, at temperatures ranging from about 25° C. to about 200° C., for a time period ranging from about 1 second to about 12 hours. After dehydration, sufficient acid to take the pH to 2–7, preferably 3–4, and preferably a solvent, is added. Then an α,β-unsaturated aldehyde or ketone of Formula II—D is added, and the resulting mixture is stirred at a temperature in the range of ambient temperature to the boiling point of the solvent, until the reaction is essentially complete.

The reaction mixture is then cooled to ambient temperature of 20°–40° C. The product is concentrated under reduced pressure and can be purified by conventional techniques such as distillation, extraction, evaporation, or column chromatography.

If desired a dehydrogenation catalyst can be added to the reaction mixture.

The dehydrogenation catalyst when employed is conventional in the art and includes metals or compounds of platinum, palladium, ruthenium, iridium, nickel, iron, copper, antimony, cobalt, rhodium, etc. The dehydrogenation metal or compound thereof deposited on a suitable support, such as alumina, carbon, clay, zeolites, chromia, zirconia, etc. A preferred dehydrogenation catalyst is palladium on carbon.

When an acid is used which is also a solvent i.e. acetic acid, no additional solvent is required.

Solvents suitable for use in the method of this invention include: water, alcohols, chlorinated hydrocarbons, hydrocarbons, aromatic hydrocarbons, ethers, organic acids, esters, and aprotic solvents such as acetonitrile. The preferred solvents are lower alkyl alcohols, such as methanol, ethanol propanol and butanol and aromatic hydrocarbons, such as benzene and toluene. The particularly preferred solvents are 1-butanol, ethanol, or toluene.

In another embodient pyridine-2,3-dicarboxylic acid derivatives containing substituents in the 4-, 5- and 6-position may conveniently be prepared by reacting, at a neutral or slightly basic pH, a Formula I—B or I—C maleate or fumarate with a substituted or unsubstituted hydroxylamine or a salt thereof, then subjecting the reaction product to dehydration using heat or a dehydrating agent or both, and subsequently adding followed by a Formula II—D α,β-unsaturated aldehyde, or ketone, at a pH of 2–7 with an acid and preferably a solvent, and stirring the resulting reaction mixture at a temperature in the range of ambient temperature to the boiling point of the solvent, and preferably at reflux, until the reaction is essentially complete and isolating the formed 4-substituted, 4,5-disubstituted, 4,6-disubstituted, 5-substituted, 6-substituted or 5-6-disubstituted pyridine-2, 3-dicarboxylic acid derivatives by standard laboratory techniques such as extraction, evaporation column chromatography, or distillation.

The amount of substituted or unsubstituted hydroxylamine or salt thereof used ranges from about 1 to about 1.5 mols of hydroxylamine per mol of said maleate or fumarate. Preferred ranges are about 1.0–1.2 mols.

If a hydroxylamine salt is used, a base such as sodium hydroxide, potassium hydroxide or ammonium hydroxide, in an amount of 1 to 2 moles, preferably 1 to 1.2 moles per mole of said hydroxylamine salt is needed to liberate the hydroxylamine.

The dehydration can be affected by heating. This dehydration by heating can be conducted with or without a suitable dehydration agent. If a agent is employed, the agent is typically present in an amount ranging from about 0.1% to about 100% weight, preferably about 0.1% to about 10% by weight. Any dehydration agent known in the art can be employed. Some suitable dehydration agent is included in Section II of this application.

The mol ratio of the alkene of Formula I—B and I—C to the aldehyde or ketone of Formula II—D is not narrowly critical and can range from about 1:1 to about 1:3. It is preferred to use approximately 1:1.0 to 1:1.3 molar ratios.

It is believed that the reaction of the I—B and I—C maleates with the substituted or unsubstituted hydroxylamine or salt thereof inherently produces the N-hydroxyamino derivatives of Formula I—D, which upon dehydration produces 2-aminobut-2-ene dioic acid derivatives.

One of the preferred embodiments of the present invention pertains to the synthesis of 2,3-pyridine-dicarboxylic acid derivative of the formula:

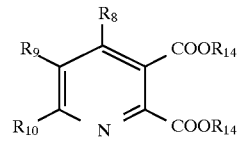

where $R_8$ is hydrogen or $C_1$–$C_6$ alkyl; $R_9$ is hydrogen, halogen, $C_1$–$C_6$ alkyl, $C_1$–$C_6$ hydroxyalkyl, $C_1$—$C_6$ alkoxy, phenyl or phenyl substituted—$C_1$–$C_6$ alkyl, or phenyl or phenyl–$C_1$–$C_6$ alkyl, each substituted by $C_1$–$C_6$ alkyl, $C_1$–$C_6$ alkoxy or halogen; $R_9$ is hydrogen, $C_1$–$C_6$ alkyl, phenyl, phenyl–$C_1$–$C_6$ alkyl, or phenyl or phenyl $C_1$–$C_6$ alkyl each substituted by one $C_1$–$C_6$ alkyl, $C_1$–$C_6$ alkoxy or halogen; $R_8$ and $R_9$ together are 1,3-butadienylene which can be substituted by halogen, $C_1$–$C_6$ alkyl, $C_1$–$C_6$ alkoxy, $C_1$–$C_6$ haloalkyl, $C_1$–$C_6$ alkylsulfonyl, nitro, cyano, phenyl, phenoxy, or phenyl or phenoxy, each substituted by one $C_1$–$C_6$ alkyl, $C_1$–$C_6$ alkyoxy or halogen, and $R_{13}$ is $C_1$–$C_6$ phenyl or $C_1$–$C_6$ phenyl alkyl; where embodiments of the compound of the preceeding formula and $R_8$, $R_9$, and $R_{10}$ substituents are as revealed and defined as corresponding substituents $R_1$, $R_2$, $R_3$, and $R_6$ of U.S. Pat. No. 4,758,667, incorporated by reference hereinto in its entirety.

Such compounds in turn are a precursor in the synthesis of compounds of the formula

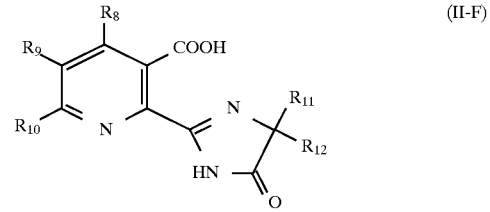

(II-F)

where $R_{11}$ and $R_{12}$ are each independently of the other $C_1$–$C_6$ alkyl, as revealed and defined as corresponding to substituents $R_4$ and $R_5$ in U.S. Pat. No. 4,758,667, incorporated hereinto by reference. The latter compound has herbicidal properties and can be used for controlling undesired plant growth.

The reactions described under Section III above are illustrated by the Examples which follow:

EXAMPLE 15

Procedure without Pd/C

Hydroxylamine free base (50% aqueous solution, 2.0 g, 30.3 mmol) is added dropwise to diethyl maleate (4.41 g, 25.6 mmol) and stirred for 60 minutes to give diethyl N-hydroxyaspartate. Toluene (25.02 g) and p-toluenesulfonic acid (0.05 g, 0.26 mmol) are added to the reaction mixture and refluxed for 4.5 hours to afford diethyl 2-aminomaleate. The reaction mixture is cooled to room temperature and added acetic acid (7.0 g) and 2-ethylacrolein (2.13 g, 25, 0 mmol). The reaction mixture is stirred at 80°–90° C. for 24 hours. It is concentrated under reduced pressure and analyzed by GLC using an external standard. The analysis showed the yield of diethyl 5-ethylpyridine-2,3-dicarboxylate is about 35%.

EXAMPLES 16–23

The procedure of Example 15 is repeated except that the following 2-aminobut-2-ene dioic acid derivatives and aldehydes or ketones are used:

| Aspartate | | Aldehyde or Ketone | | |
|---|---|---|---|---|
| $R_{15}OOC-C=CH-COOR_{16}$ | | $R_9-C=CHR_8$ | | |
| \|  | | \| | | |
| $NH_2$ | | $R_{10}-C=O$ | | |
| $R_{15}$ | $R_{16}$ | $R_9$ | $R_{10}$ | $R_8$ |
| Example 16 | methyl | propyl | H | H | phenyl |
| Example 17 | propyl | propyl | phenyl | ethyl | methyl |
| Example 18 | butyl | butyl | ethyl | methyl | H |
| Example 19 | ethyl | ethyl | methyl | H | H |
| Example 20 | ethyl | ethyl | H | methyl | H |
| Example 21 | ethyl | ethyl | H | H | methyl |
| Example 22 | ethyl | ethyl | $(CH_2)_3$ | | H |
| Example 23 | ethyl | ethyl | $(CH_2)_4$ | | H |

IV. Preparation of Quinoline Derivatives by Reacting a Substituted or Unsubstituted Phenylhydroxylamine with a Substituted or Unsubstituted Diacid Derivative to Form a Phenylhydroxylamine Adduct, Dehydrating to Form Substituted and Unsubstituted 2-Anilino-But-2-Ene Dicarboxylic Acid Derivative, Followed by Reaction with Vilsmeier Reagent to Form a Quinoline Derivative The reaction descriptions which follow actually are preferred embodiments fall under the subject matter described in Section I above, wherein the substituted or unsubstituted hydroxylamine is a phenylhydroxylamine which may have substituent groups on the aromatic ring.

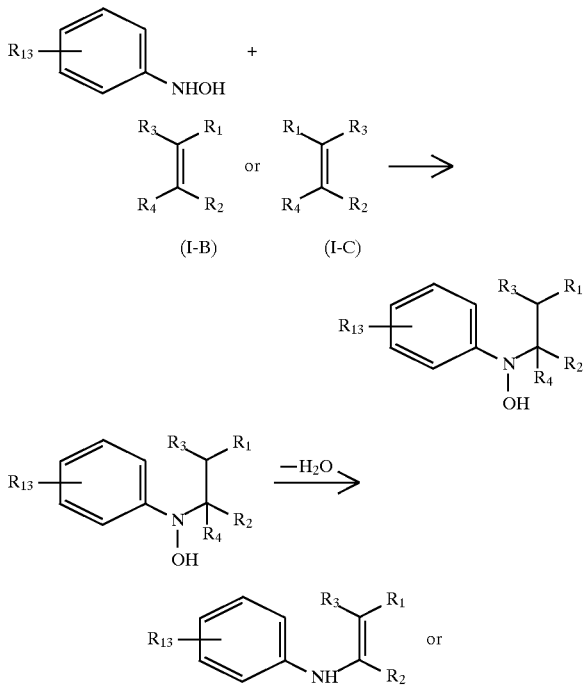

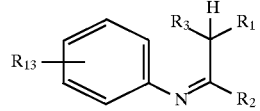

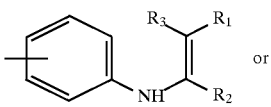

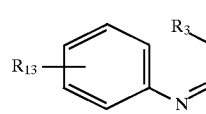

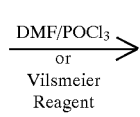

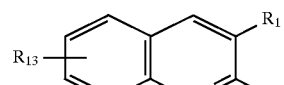

wherein $R_1$, $R_2$, $R_3$, and $R_4$ are as described in Section III above;

wherein $R_{13}$ is H, alkyl (preferably $C_1$–$C_6$ straight or branched, aryl (preferably phenyl or naphthyl), alkoxy, halogen, cyano, carboalkoxy, thioalkoxy, or $CF_3$.

The reaction conditions fall within the ranges previously provided in Section I and Section II above, and the following examples are provided for purposes of illustration.

EXAMPLE 24

Synthesis of N-Phenylhydroxylamine

Prepared by the method of O. Kamm, Organic Synthesis, Vol.1, pages 445–447 the crude product was dissolved in ether filtered free of salts. The solvent was partially evaporated and hexane added. The resultant white material was dried in vacuum oven mp. 82°–84° C.

EXAMPLE 25

Synthesis of Diethyl-N-Phenyl-N-Hydroxyaspartate

Diethylmaleate (7.7 g, 0.045 mole) was added to a mixture containing 5.0 g (0.046 mole) N-phenylhydroxylamine in 7.66 g of absolute ethanol. The mixture was allowed to stir for 15 hours at room temperature. GC analysis showed a trace of diethylmaleate remaining. 1.0 g of Norite was added along with 10 ml of additional ethanol. The mixture was allowed to stir for 10 minutes and then filtered free of the carbon. The carbon was washed with additional ethanol. The filtrate was evaporated under high vacuum temperature to give an oil which crystallized upon cooling in a dry ice/acetone bath. 11.9 g obtained after drying in vacuum desicator at room temperature under high vacuum mp 50°–53° C.

EXAMPLE 26

Preparation of Diethyl-N-Phenyl-N-Hydroxyaspartate

A solution of diethyl maleate (20.65 g, 0.117 mol) in ethanol (25.0 g) was added dropwise to a solution of N-phenylhydroxylamine (14.6 g, 0.129 mol) in ethanol (46.3 g). The reaction mixture was stirred at room temperature for an hour. The analysis of the reaction mixture by thin layer chromatography indicated the completion of the reaction. The reaction mixture was concentrated under reduced pressure to give the crude product (37.46 g). The crude product was crystallized from ethylacetate-hexane (28.0 g, 85.0% yield).

EXAMPLE 27

Preparation of Diethyl 2-Anilinobut-2-ene-2,3-dicarboxylate 2.81 g (0.01 mole) of diethyl N-phenyl-N-hydroxy aspartate was dissolved in 20 ml chloroform. To this solution was added 1.8 g (0.018 mole) of triethylamine. To this solution, 1.0 g (0.0125 mole) acetyl chloride was added at room temperature, 22°–25° C. This mixture was allowed to stir for 30 minutes before 1.8 g (0.018 mole) of triethylamine was added. The resultant solution was heated to 55° C. for 4 hours. L.C. shows conversion to diethyl-N-phenylaminomaleate.

EXAMPLE 28

Preparation of Diethyl 2-Anilinobut-2-ene-2,3-dicarboxylate

Triethylamine (4.02 g, 0.0398 mol) was added to a solution of diethyl N-phenyl-N-hydroxyaspartate (10.1 g, 0.0357 mol) in dichloromethane (40 mL) and stirred for 15 minutes. Acetic anhydrode (4.10 g, 0.040 mol) was added to reaction mixture over a period of 10 minutes. The reaction mixture was stirred at room temperature for an hour and refluxed for another hour. The reaction mixture was concentrated under reduced pressure to give the crude product. The crude product was purified by distillation to give diethyl 2-anilinobut-2-ene-2,3-dicarboxylate (7.8 g, 74% yield). NMR (CDCl$_3$) δ1.03 (t, J 7.2 Hz, 3H), 1.29 (t, J 7.2, 3H), 4.18 (m, 4H), 5.38 (s, 1H), 6.90–7.31 (m, 5H).

EXAMPLE 29

Preparation of Diethyl Quinoline-2,3-dicarboxylate

The Vilsmeier reagent is prepared by adding Diphosgene (3.8 g, 19.3 mmol) dropwise to a mixture containing dimethyl foramide (2.75 g, 37.7 mmol) and dichloroethane (50 mL) while the temperature is maintained below 20° C. using an ice bath. The reaction mixture is stirred for 45 minutes at room temperature. Then a solution of diethyl 2-anilinobut-2-ene-2,3-dicarboxylate (4.5 g, 17.1 mmol) in dichloroethane (20 mL) is added dropwise to the reaction mixture and stirred at 80°–84° C. for 2.5 hours. The reaction mixture is cooled to room temperature and diluted with ethyl acetate (250 mL). The reaction mixture is washed twice with brine (50 mL each) and once with water (100 mL). The organic layer is concentrated under reduced pressure to give the crude product which is purified by crystallization using ethyl acetate and hexane to give diethyl quinoline-2,3-dicarboxylate (2.9 g, 62% yield).

The above-described preferred embodiments are intended to be illustrative of the process of the present invention, as one skilled in the art can introduce modifications which provide equivalent functions and which are intended to fall within the scope of the present invention as defined by the claims which follow.

We claim:
1. A method for the preparation of quinoline derivatives of the formula:

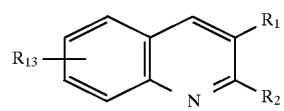

wherein R$_1$ and R$_2$ are each independently

wherein Z is OR$_5$ or NR$_5$R$_6$; or
CN; or wherein R$_1$ and R$_2$ together is

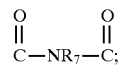

wherein R$_5$ and R$_6$ are each independently H, alkyl, aryl, arylalkyl; or
wherein R$_5$ and R$_6$ together with the nitrogen atom form a heterocyclic substituent, selected from pyrrolidinyl, piperidinyl, imidazolidyl, and hydrogenated pyrimidinyl;
wherein R$_7$ is H, alkyl, aryl, or an alkoxy of 1–6 carbon atoms;
wherein R$_{13}$ is H, alkyl, aryl, alkylaryl, alkoxy, halogen, cyano, carboalkoxy, thioalkoxy, or CF$_3$;
which method comprises the steps of:
  a) providing an unsaturated diacid derivative of the formula:

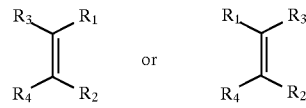

or an isomer thereof, wherein R1 and R2 are defined above, and wherein R3 and R4 are each independently H; alkyl; unsubstituted aryl; aryl having substituents selected from alkyl, arylalkyl, alkoxy, carboxy, halogen, nitro and cyano;

wherein Z is as defined above; CN; or halogen;
  b) contacting said unsaturated diacid derivative with a substituted or unsubstituted phenylhydroxyalmine of the formula:

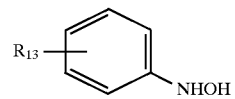

wherein R$_{13}$ is as defined above, or a suitable salt thereof, in a reaction medium having a pH ranging from about 5 to about 12, whereby a substituted or unsubstituted N-phenyl-N-hydroxy-2-aminobutane dicarboxylic acid derivative is produced;
  c) dehydrating said N-phenyl-N-hydroxy-2-aminobutane dicarboxylic acid derivative, using heat or a dehydrating agent, or both, whereby substituted or unsubstituted 2-anilinobut-2-ene dicarboxylic acid derivative is produced; and
  d) reacting said-2-anilinobut-2-enedicarboxylic acid derivative with a Vilsmeier reagent, whereby a quinoline derivative is produced.

2. A method according to claim 1 wherein $R_{13}$ is selected from hydrogen and a $C_1$ to $C_6$ alkyl.

3. A method according to claim 1 wherein said diacid derivative is selected from the group consisting of diethyl maleate, dimethyl maleate, dibutyl maleate, dimethyl fumarate, diethyl fumarate, dibutyl fumarate, fumaronitrile, and triethylethanetricarboxylate.

4. A method according to claim 1, wherein said pH in step (b) is from about 6.5 to about 9.

5. A method according to claim 1, wherein said reaction medium in step (b) includes a solvent selected from the group consisting of water, a $C_1$13 $C_6$ alkanol, a halogenated $C_1$–$C_6$ hydrocarbon, an aromatic hydrocarbon, an ether, an ester, an aprotic solvent, and mixtures thereof.

6. A method according to claim 1, wherein step (c) is effected in the presence of a dehydrating agent selected from inorganic acids, ion exchange acidic resins, organic acids, inorganic bases, organic bases, basic ion exchange resins, transition metal catalysts, and acylation agents, the acylation agents optionally in combination with an organic base.

7. A method according to claim 1, wherein the dehydration in step (c) is effected in a solvent selected from water, alcohols, hydrocarbons, halogenated hydrocarbons, aromatic hydrocarbons and polar aprotic solvents, at a temperature of from 25° C. to 300° C.

8. A method according to claim 1, wherein the Vilsmeier reagent is prepared from diphosgene and dimethylformamide.

9. A method according to claim 1, wherein said Vilsmeier reagent is prepared from phosphorous oxychloride and dimethylformamide.

* * * * *